(12) United States Patent
Igarashi et al.

(10) Patent No.: US 6,764,841 B2
(45) Date of Patent: Jul. 20, 2004

(54) PRODUCTION PROCESS OF GLUCOSE-1-PHOSPHATE

(75) Inventors: Kazuaki Igarashi, Haga-gun (JP); Katsuya Ozaki, Haga-gun (JP)

(73) Assignee: Kao Corporation, Tokyo (JP)

( * ) Notice: Subject to any disclaimer, the term of this patent is extended or adjusted under 35 U.S.C. 154(b) by 126 days.

(21) Appl. No.: 10/053,550

(22) Filed: Jan. 24, 2002

(65) Prior Publication Data

US 2002/0150998 A1 Oct. 17, 2002

(30) Foreign Application Priority Data

Feb. 2, 2001 (JP) .......................... 2001-027055
Sep. 28, 2001 (JP) .......................... 2001-303745

(51) Int. Cl.$^7$ .......................... C12P 19/02; C12P 19/00
(52) U.S. Cl. .......................... 435/105; 435/72; 435/74
(58) Field of Search .......................... 435/105, 74, 72

(56) References Cited

U.S. PATENT DOCUMENTS

| | | | |
|---|---|---|---|
| 3,303,101 A | 2/1967 | Kinoshita et al. | |
| 4,787,940 A | 11/1988 | Kayane et al. | |
| 5,543,310 A | 8/1996 | Kayane et al. | |

FOREIGN PATENT DOCUMENTS

| | | |
|---|---|---|
| GB | 1 321 076 | 6/1973 |
| JP | 10-14580 | 1/1988 |
| JP | 63-208594 | 8/1988 |

OTHER PUBLICATIONS

Weinhäusel et al, Appl. Microbiol. Biotechnol. 41:510–516 (1994).*

B. Nidetzky, et al., "Maltodextrin Phosphorylase from *Escherichia coli*: Production and Application for the Synthesis of Alpha–Glucose–1–Phosphate", Annals New York Academy of Sciences, pp. 208–218, 1996.

A. Weinhaeusel, et al., "Application of *Escherichia coli* Maltodextrin–Phosphorylase for the Continuous Production of Glucose–1–Phosphate", Enzyme Microb. Technol., 1995, vol. 17, Feb., pp. 140–146.

D. Linder, et al., "1,4–Alpha–Glucan Phosphorylase from Klebsiella Pneumoniae Purification, Subunit Structure and Amino Acid Composition", Eur. J. Biochem., 70, 291–303, (1976).

A. Weinhaeusel, et al., Biochem. J., vol. 326, XP–002198495, pps. 773–783, "α–1,4–D–Glucan Phosphorylase of Gram–Positive Corynebacterium Callunae: Isolation, Biochemical Properties and Molecular Shape of the Enyzme from Solution X–Ray Scattering", 1997.

A. Weinhausel, et al., Enzyme and Microbial Technology, vol. 17, pp. 140–146, "Application of *Escherichia coli* Maltodextrin–Phosphorylase for the Continuous Production of Glucose–1–Phosphate", 1995.

B. Nidetzky, et al., J. Carbohydrate Chemistry, vol. 14, No. 7, pp. 1017–1028, "Enzymatic Synthesis of α–Glucose–1–Phosphate: A Study Employing a New α–1,4 Glucan Phosphorylase from Corynebacterium Callunae", 1995.

H–J. Shin, et al., Journal of Industrial Microbiology & Biotechnology, vol. 24, pp. 89–93, "Formation of α–D–Glucose–1–Phosphate by Thermophilic α–1,4–D–Glucan Phosphorylase", 2000.

T. Kamogashira, et al., J. Ferment, Technol., vol. 66, No. 6, pp. 649–655, "Isolation of a Fosfomycin–Hypersensitive Mutant and Production of α–D–Glucose–1–Phosphate from Bacillus sp. BA–3796 Screened by Its use", 1988.

* cited by examiner

Primary Examiner—Francisco Prats
(74) Attorney, Agent, or Firm—Oblon, Spivak, McClelland, Maier & Neustadt, P.C.

(57) ABSTRACT

The invention relates to a process for producing glucose-1-phosphate, which contains the steps of culturing bacteria of the genus Corynebacterium in a medium containing a saccharide and at least 1 mM of phosphoric acid or a derivative or salt thereof, and collecting glucose-1-phosphate produced and accumulated in the medium.

A mass of G-1-P can be provided without conducting complicated steps which are required of the enzymatic process.

19 Claims, No Drawings

PRODUCTION PROCESS OF GLUCOSE-1-PHOSPHATE

BACKGROUND OF THE INVENTION

1. Field of the Invention

The present invention relates to a process for producing glucose-1-phosphate making use of microorganisms.

2. Description of the Background Art

Glucose-1-phosphate (hereafter abbreviated as "G-1-P") is useful as a substrate for syntheses of drugs and saccharides.

G-1-P is mainly obtained by phosphorolysis of starch or dextrin with maltodextrin phospholylase (MDPase), and a process making use of MDPase derived from potato (Japanese Patent Publication No. 95942/1994) and the so-called enzymatic process using MDPase derived from microorganisms have been reported to date.

As examples of the enzymatic process using MDPase derived from microorganisms, have been reported a process using an enzyme derived from *Escherichia coli* (Enzyme Microb. Technol. 17, 140–146 (1995) and a process using an enzyme derived from *Corynebacterium callunae* (J. Carbohydrate Chem., 14,1017–1028 (1995)). More recently, processes for producing G-1-P making use of heat-stable MDPase derived from medium thermophilic bacteria and high thermophilic bacteria such as *Bacillus stearothermophilus* (Japanese Patent Application Laid-Open No. 14580/1998) and *Thermus caldophilus* (J. Industrial Microbiol., 24, 89–93 (2000)) have been reported.

However, such enzymatic processes using the enzyme itself require complicated steps such as a step of extracting an enzyme from plants or bacteria and preparation of an immobilized enzyme, and it has hence been desirable to develop a simpler process for producing G-1-P.

SUMMARY OF THE INVENTION

It is an object of the present invention to provide a process for producing G-1-P by which a mass of G-1-P can be provided without using complicated steps.

The present inventors have carried out various investigations as to bacteria producing a mass of G-1-P in a medium by culture. As a result, it has been found that when bacteria of the genus Corynebacterium are cultured under conditions of the presence of a saccharide and a high concentration of phosphoric acid or a derivative thereof, a high concentration of G-1-P can be produced directly in a medium to produce a mass of G-1-P.

According to the present invention, there is thus provided a process for producing glucose-1-phosphate, comprising the steps of culturing bacteria of the genus Corynebacterium in a medium containing a saccharide and at least 1 mM of phosphoric acid or a derivative or salt thereof, and collecting glucose-1-phosphate produced and accumulated in the medium.

DETAILED DESCRIPTION OF THE PREFERRED EMBODIMENTS

The bacteria of the genus Corynebacterium used in the present invention are not particularly limited so far as they belong to the genus Corynebacterium and produce G-1-P in a medium in the presence of a saccharide and a fixed concentration of phosphoric acid or a derivative or salt thereof, and examples thereof include *Corynebacterium callunae*, *Corynebacterium glutamicum*, *Corynebacterium vitaeruminis* and *Corynebacterium pilosum*. Among these, *Corynebacterium callunae*, *Corynebacterium glutamicum* and *Corynebacterium vitaeruminis* are preferred, with *Corynebacterium callunae* IFO 15359, *Corynebacterium glutamicum* JCM 1321 and *Corynebacterium vitaeruminis* JCM 1323 strains being particularly preferred.

Preferable examples of the saccharide added to the medium include monosaccharides, disaccharides, oligosaccharides and polysaccharides containing glucose as a constitutive saccharide, and α-1,4-glucane-containing saccharides, for example, starch, amylose, dextrin, maltose, maltooligosaccharides, amylopectin and glycogen are mentioned as more preferable examples. Among these, cheap starch, dextrin and maltooligosaccharides are particularly preferred.

Such saccharides may be used either singly or in any combination thereof.

Examples of the derivative or salt of phosphoric acid to be added to the medium include metaphosphoric acid, tripolyphosphoric acid, polyphosphoric acid, diphosphoric acid, polymetaphosphoric acid, phosphates and salts of these derivatives. As the salts, are preferred sodium and potassium salts. Examples of particularly preferred phosphates include monopotassium phosphate, dipotassium phosphate, monosodium phosphate and disodium phosphate. In the present invention, it is preferable to use a mixture of phosphoric acid or a derivative thereof and a salt thereof, or a mixture of a few kinds of phosphates or salts of the derivatives.

The concentration of phosphoric acid, or the derivative or salt thereof in the medium must be at least 1 mM from the viewpoint of the effect, and it is desirable that the concentration be in a range of preferably 1 mM to 1 M, more preferably 5 mM to 500 mM, particularly preferably 100 mM to 500 mM.

The medium used in the present invention is not particularly limited so far as bacteria of the genus Corynebacterium can grow therein, and a medium containing a carbon source, a nitrogen source, metal minerals, vitamins, etc. in addition to the above-described saccharide and phosphoric acid or the derivative or salt thereof may be used.

Examples of other carbon sources than the saccharide include organic acid salts such as acetates.

Examples of the nitrogen source include ammonia, inorganic and organic ammonium salts such as ammonium chloride, ammonium sulfate, ammonium nitrate, ammonium carbonate, ammonium phosphate and ammonium acetate, and nitrogen-containing organic substances such as urea, peptone, meat extracts, yeast extracts and hydrolyzates of casein, and amino acids such as glycine, glutamic acid, alanine and methionine.

Examples of the metal minerals include sodium chloride, ferrous sulfate, magnesium sulfate, manganese sulfate, zinc sulfate and calcium carbonate. These metal minerals may be used either singly or in any combination thereof as needed.

The culture is conducted by suitably adjusting pH and temperature so as to become conditions under which the microorganisms can sufficiently grow. However, it is generally preferred that the culture be conducted for 12 to 96 hours at a pH of 5 to 8 and a temperature of 25 to 400° C.

As a culturing method, a resting-bacterial reaction and an immobilized-bacterial reaction may also be used in addition to shaking culture and culture by a fermentor.

The collection of G-1-P produced and accumulated in the medium may be conducted by, for example, separating and removing the bacteria used and combining centrifugation, ultrafiltration, ion exchanging, reverse osmosis, electrodialysis, salting out, crystallization etc. with one another in accordance with a publicly known method.

According to the process of the present invention, a high concentration of G-1-P can be thus produced directly in the medium, and so a mass of G-1-P can be produced without conducting any complicated steps compared with the enzymatic process using an enzyme. As demonstrated in Examples, which will be described subsequently, such an effect is scarcely recognized in the MDPase derived from bacteria of the genus Bacillus (Japanese Patent Application Laid-Open No. 14580/1998) in which the MDPase is contained in the bacteria like the bacteria of the genus Corynebacterium, and the specific activity thereof is 4.2 U/mg and comparable with MDPase derived from the bacteria of the genus Corynebacterium the specific activity of which is 5.3 U/mg (J. Carbohydrate Chem., 14, 1017–1028 (1995)), and is a characteristic effect of the bacteria of the genus Corynebacterium.

<Determination of G-1-P>

The determination of G-1-P was conducted in accordance with the Weinhausle's method (Enzyme Microb. Technol., 17, 140–146 (1995)) with the method modified.

More specifically, an enzymatic reaction solution (100 μL, containing 100 mM Tris-acetate buffer (pH 6.8), 2 mM EDTA, 10 mM magnesium sulfate, 2 mM NAD, 10 μM glucose-1,6-diphosphate, 1.2 U/mL phosphoglucomutase (derived from rabbit muscle, product of Roche Diagnostic Co.) and 1.2 U/mL glucose-6-phosphate dehydrogenase (derived from *Leuconostoc mesenteroides*, product of Roche Diagnostic Co.)) was added to a sample (100 μL) suitably diluted on a 96-well microplate, and the mixture was incubated at 37° C. for 30 minutes to measure an absorbance at 340 nm.

EXAMPLE 1

One platinum loop of *Corynebacterium callunae* IFO 15359, *Bacillus subtilis* IFO 3037, *Bacillus subtilis* IFO 1372 or *Bacillus licheniformis* JGM 2505 was inoculated into a medium (containing 3.5% soluble starch, 3.0% Lablemco powder (product of OXOID Co.), 0.05% magnesium sulfate, 0.04% monopotassium phosphate and 0.1% disodium phosphate) to conduct shaking culture overnight at 30° C. as species culture.

Each (1%) of the species bacteria cultured above was inoculated on a medium prepared by adding a potassium phosphate buffer (pH 7.0) to 3.5% soluble starch, 3.0% Lablemco powder (product of OXOID Co.), 0.05% magnesium sulfate so as to give a phosphate concentration of 10 mM, 20 mM or 40 mM to conduct culture at 30° C. for 5 days as principal culture. The concentration of G-1-P in a supernatant thus obtained was determined. The results are shown in Table 1.

TABLE 1

| Concentration of phosphate | Productivity of G-1-P (g/L) | | |
| --- | --- | --- | --- |
| | 10 mM | 20 mM | 40 mM |
| C. callunae IFO 15359 | 0.15 | 0.41 | 0.58 |
| B. subtilis IFO 3037 | <0.01 | <0.05 | <0.01 |
| B. subtilis IFO 1372 | 0.03 | <0.01 | <0.01 |
| B. licheniformis JGM 2505 | 0.07 | 0.01 | 0.01 |

EXAMPLE 2

One platinum loop of *Corynebacterium callunae* IFO 15359, *Corynebacterium glutamicum* JCM 1321, *Corynebacterium vitaeruminis* JCM 1323, *Bacillus subtilis* IFO 3037, *Bacillus subtilis* IFO 1372 or *Bacillus licheniformis* JGM 2505 was inoculated into a medium (containing 3.5% soluble starch, 3.0% Lablemco powder (product of OXOID Co.), 0.05% magnesium sulfate, 0.04% monopotassium phosphate and 0.1% disodium phosphate) to conduct shaking culture overnight at 30° C. as species culture.

The species bacteria cultured above were respectively collected, and each of them was inoculated on a medium prepared by adding a potassium phosphate buffer (pH 7.0) to 0.67% yeast nitrogen base (product of Difco Co.) and 10% dextrin (derived from potato, product of SIGMA Co.) so as to give a phosphate concentration of 100 mM, 200 mM, 400 mM or 500 mM in such a manner that $OD_{600\ nm}$ is 10, thereby conducting culture at 30° C. for 5 days as principal culture. The concentration of G-1-P in a supernatant thus obtained was determined. The results are shown in Table 2.

TABLE 2

| Concentration of phosphate | Productivity of G-1-P (g/L) | | | |
| --- | --- | --- | --- | --- |
| | 100 mM | 200 mM | 400 mM | 500 mM |
| C. callunae IFO 15359 | 2.1 | 5.1 | 12.7 | 12.7 |
| C. glutamicum JCM 1321 | — | — | 11.5 | — |
| C. vitaeruminis JCM 1323 | — | — | 13.0 | — |
| B. subtilis IFO 3037 | 0.01 | 0.02 | — | 0.04 |
| B. subtilis IFO 1372 | 0.02 | 0.03 | — | 0.02 |
| B. licheniformis JGM 2505 | 0.01 | 0.01 | — | 0.01 |

As a result of the above, G-1-P was able to be produced with good efficiency depending on concentration by using the bacteria of the genus Corynebacterium and adjusting the concentration of the phosphate.

According to the process of the present invention, as described above, a mass of G-1-P can be provided without conducting complicated steps such as a step of extracting an enzyme from plants or bacteria and preparation of an immobilized enzyme, which are required of the enzymatic process.

What is claimed is:

1. A process for producing glucose-1-phosphate, comprising the steps of culturing bacteria of the genus Corynebacterium in a medium containing a saccharide and at least 1 mM of phosphoric acid or a derivative or salt thereof, and collecting glucose-1-phosphate produced and accumulated in the medium.

2. The process according to claim 1, wherein the bacteria of the genus Corynebacterium are selected from *Corynebacterium callunae*, *Corynebacterium glutamicum* and *Corynebacterium vitaeruminis*.

3. The process according to claim 2, wherein the bacterial of the genus Corynebacterium are selected from *Corynebacterium callunae* IFO 15359, *Corynebacterium glutamicum* JCM 1321 and *Corynebacterium vitaeruminis* JCM 1323 strains.

4. The process according to claim 1, wherein the saccharide is at least one selected from monosaccharides, disaccharides, oligosaccharides and polysaccharides containing glucose as a constitutive saccharide.

5. The process according to claim 1, wherein the concentration of phosphoric acid, or the derivative or salt thereof is in the range of from 1 mM to 1 M.

6. The process according to claim 1, wherein the saccharide is an α-1,4-glucane-containing saccharide.

7. The process according to claim 6, wherein the α-1,4-glucane-containing saccharide is selected from the group consisting of starch, amylose, dextrin, maltose, maltooligosaccharides, amylopectin, and glycogen.

8. The process according to claim 1, wherein the phosphoric acid or a derivative or salt thereof is selected from the group consisting of metaphosphoric acid, tripolyphosphoric acid, polyphosphoric acid, diphosphoric acid, and polymetaphosphoric acid, and phosphates or salts thereof.

9. The process according to claim 1, wherein the phosphoric acid is in a salt form selected from a sodium salt or a potassium salt.

10. The process according to claim 9, wherein the salt form of the phosphoric acid is selected from the group consisting of monopotassium phosphate, dipotassium phosphate, monosodium phosphate, and disodium phosphate.

11. The process according to claim 1, wherein the concentration of phosphoric acid, or the derivative or salt thereof is in the range of from 5 mM to 500 mM.

12. The process according to claim 1, wherein the concentration of phosphoric acid, or the derivative or salt thereof is in the range of from 100 mM to 500 mM.

13. The process according to claim 1, wherein said medium further comprises at least one additive selected from the group consisting of a carbon source, a nitrogen source, a metal mineral, and a vitamin.

14. The process according to claim 1, wherein said medium further comprises acetate.

15. The process according to claim 1, wherein said medium further comprises at least one nitrogen source selected from the group consisting of ammonia, ammonium chloride, ammonium sulfate, ammonium nitrate, ammonium carbonate, ammonium phosphate, ammonium acetate, urea, peptone, meat extract, yeast extract, hydrolyzate of casein, glycine, glutamic acid, alanine, and methionine.

16. The process according to claim 1, wherein said medium further comprises at least one metal selected from the group consisting of sodium chloride, ferrous sulfate, manganese sulfate, zinc sulfate, and calcium carbonate.

17. The process according to claim 1, wherein said culturing is for 12 to 96 hours at a pH of 5 to 8 and at a temperature of 25 to 40° C.

18. The process according to claim 1, wherein said culturing is a method selected from the group consisting of resting-bacterial reaction, immobilized bacterial reaction, shaking culture by fermentor.

19. The process according to claim 1, wherein said collected comprises a method selected from the group consisting of centrifugation, ultrafiltration, ion exchanging, reverse osmosis, electrodialysis, salting out, and crystallization.

* * * * *

UNITED STATES PATENT AND TRADEMARK OFFICE
CERTIFICATE OF CORRECTION

PATENT NO.    : 6,764,841 B2
DATED         : July 20, 2004
INVENTOR(S)   : Kazuaki Igarashi et al.

It is certified that error appears in the above-identified patent and that said Letters Patent is hereby corrected as shown below:

Column 4,
Line 54, "bacterial" should read -- bacteria --

Column 6,
Line 20, "shaking culture by fermentor" should read -- shaking culture, culture by fermentor --
Line 22, "collected" should read -- collecting --

Signed and Sealed this

Seventh Day of December, 2004

JON W. DUDAS
*Director of the United States Patent and Trademark Office*